United States Patent
Gupta et al.

(10) Patent No.: US 6,721,049 B1
(45) Date of Patent: Apr. 13, 2004

(54) DEVICE FOR EFFICIENT LIGHT COLLECTION FROM A SAMPLE

(75) Inventors: Neelam Gupta, Bethesda, MD (US); Rachid Dahmani, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/532,851

(22) Filed: Mar. 22, 2000

(51) Int. Cl.$^7$ .................................................. G01J 3/28
(52) U.S. Cl. ...................................................... 356/326
(58) Field of Search ................................ 356/326, 311, 356/317, 335–340

(56) References Cited

U.S. PATENT DOCUMENTS 5,089,714 A * 2/1992 Ludlow et al. ............. 250/574
5,650,847 A * 7/1997 Maltsev et al. ............. 356/336
6,399,026 B1 * 6/2002 Karrai ........................ 250/234

FOREIGN PATENT DOCUMENTS

EP 864898 A1 * 9/1998
JP 11-230823 A * 8/1999

* cited by examiner

*Primary Examiner*—Zandra V. Smith
(74) *Attorney, Agent, or Firm*—Mark D. Kelly; William V. Adams

(57) ABSTRACT

A spectrometric or photo-detector device accessory for illumination of a sample and highly efficient collection of light therefrom includes an ellipsoidal mirror having focal points $f_1$ and $f_2$; a first optical fiber leg having a terminus positioned at or near $f_1$ and containing fibers for conveying light to $f_1$ and collecting light emitted from a sample positioned at $f_1$, a second optical fiber having a terminus positioned at or near $f_2$, for collecting light reflected by the mirror and focussed at $f_2$ and a rigid stand for holding the mirror and fiber optic cables in fixed alignment.

11 Claims, 2 Drawing Sheets

DEVICE FOR EFFICIENT LIGHT COLLECTION FROM A SAMPLE

BACKGROUND OF THE INVENTION

1. Field of the Invention

The invention relates in general to spectrometric devices for efficient collection of light for analysis. More particularly, the invention relates to a light collecting mirror and optical fiber device for use in spectrum analysis.

2. Background of the Invention

In a light scattering experiment, scattered light is usually emitted in a $4\pi$ solid angle and collected with an optical element such as a lens, mirror, or fiber. Only a fraction of the light is actually collected, however, because the solid angle intercepted by such an optical element is relatively small. Typical examples of such devices are shown in U.S. Pat. No. 5,680,209 entitled "Spectroscopic systems for the analysis of small and very small quantities of substances." To increase the collection efficiency of light emanating from a sample, a light collecting device is needed that allows for optimal detection of the emitted light for spectrometric analysis. The present invention fulfills this need by providing a fiber optic/mirror device that is easy to use in both laboratory and field applications and provides for both the delivery of light to a sample and the optimal collection of light from the sample.

SUMMARY AND ADVANTAGES OF THE INVENTION

The invention relates to a device for efficient delivery of light to a sample and collection of most of the light scattered from the sample. The device comprises an ellipsoidal mirror, and several optical fiber legs that can be bundled together that illuminate the observed sample and collect light from the sample. The sample, residing either within a capillary tube or sample chamber, is placed at a first focal point of the ellipsoidal mirror along with a first leg of a light delivery and collection optical fiber. The light emitted in the solid angle facing this leg is collected by the fibers that comprise the leg. The remaining light is reflected by the inner surface of the ellipsoidal mirror, directed and focused at the second focal point of the ellipsoidal mirror, and provides additional light collection from the sample at a terminus of a second optical fiber leg positioned at the second focal point. Thus, most of the scattered light from the sample is collected by these two optical fiber collecting legs located at the focal points of the ellipsoidal mirror.

The mirror/optical fiber collection device can be used in either a laboratory or field application for very efficient light collection from a sample. Efficient light collection is critical, particularly in situations where very low light levels are observed or where scattering phenomena exists having a low cross section, such as in Raman scattering measurements. Accordingly, a system in accordance with the present invention provides a rugged and portable light collecting device using optical fibers for efficient delivery and collection of light for spectrometric applications. Moreover, a system in accordance with the present invention provides a device that is capable of more efficient radiation collection capability compared to presently used schemes of collecting light, and, at the same time is portable and inexpensive to produce and can be used in fluorescence, Raman, emission, and absorption spectral measurement based systems. Still further advantages will become apparent from consideration of the ensuing detailed description.

BRIEF DESCRIPTION OF THE DRAWINGS

In the drawings, like numerals indicate like parts.

DETAILED DESCRIPTION

Figure 1:
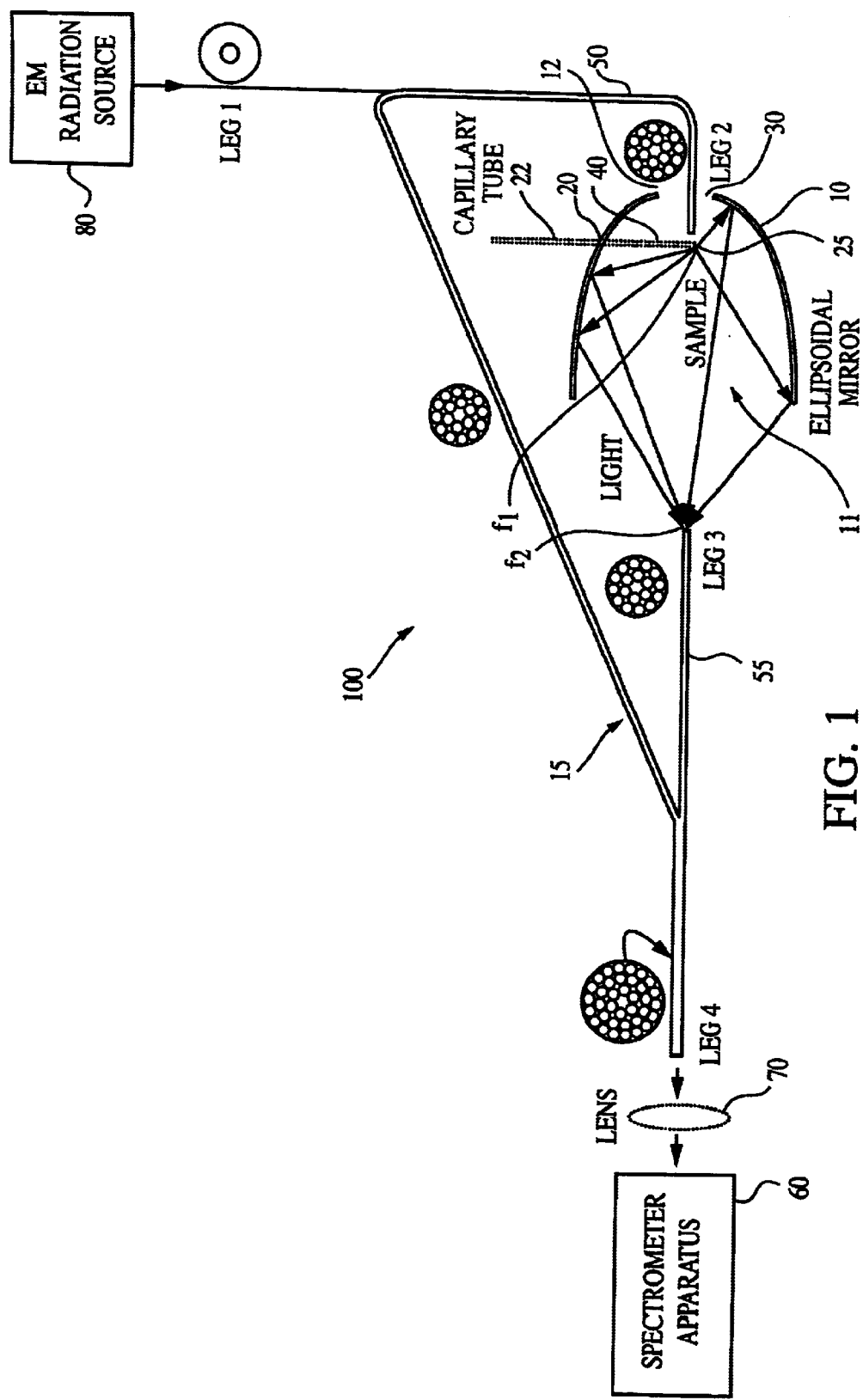
FIG. 1 shows an exemplary representation of a light collector device according to the present invention.

FIG. 1 shows an exemplary representation of a light collecting device 100 in accordance with the present invention and generally comprised of an ellipsoidal mirror 10 and a multi-legged optical fiber bundle 15. Ellipsoidal mirror 10 has an open end 11 and a closed end 12, two focal points, $f_1$ and $f_2$, which define an optical axis, and ports or apertures 20 and 30. Ellipsoidal mirror 10 could also be closed on both ends. Port 20 is a small opening in a sidewall of the mirror and allows for the insertion of a sample holder 40, in this case a capillary tube, so that a sample 25 can be positioned at the focal point $f_1$ of ellipsoidal mirror 10. Port 20 is shown as an aperture at the top of mirror 10 directly above $f_1$ to enable insertion of capillary tube 22 in a direction orthogonal to the optical axis of mirror 10 and allows for placement of sample 25 at $f_1$. A second port 30 is an opening positioned along the optical axis at the closed end 12 of ellipsoidal mirror 10 and allows for insertion of an optical fiber bundle 50. Optical fiber bundle 50 forms Leg 2 and delivers the excitation light to the sample 25 from EM radiation source 80 and also collects the light scattered from behind sample 25. The tip of optical fiber bundle 50 should be positioned as close to sample 25 and $f_1$ as is practical. Alternatively, a small focal length lens may be positioned between fiber and sample.

Another optical fiber bundle 55 forming Leg 3 is placed at the second focal point $f_2$ of mirror 10, for collecting the light scattered from the sample and reflected from the internal surfaces of the mirror 10 and focused at $f_2$. The collection fibers in Legs 2 and 3 are preferably bundled together to deliver the scattered light to the spectrometric apparatus 60 through lens 70, (note that either a collimating or Grin lens can be used depending upon spectrometric application). Alternatively, the light focused at $f_2$ can include a convex lens 65 for more efficient transmission of scattered light into the optical fibers 55 of Leg 3. Spectrometric device 60 can be replaced with a photo-detector device for other applications. The optical fiber bundle comprising Leg 1 provides excitation light to the sample. Leg 1 can be bundled with the optical fiber Leg 2 in a common bundle configuration.

Figure 2:
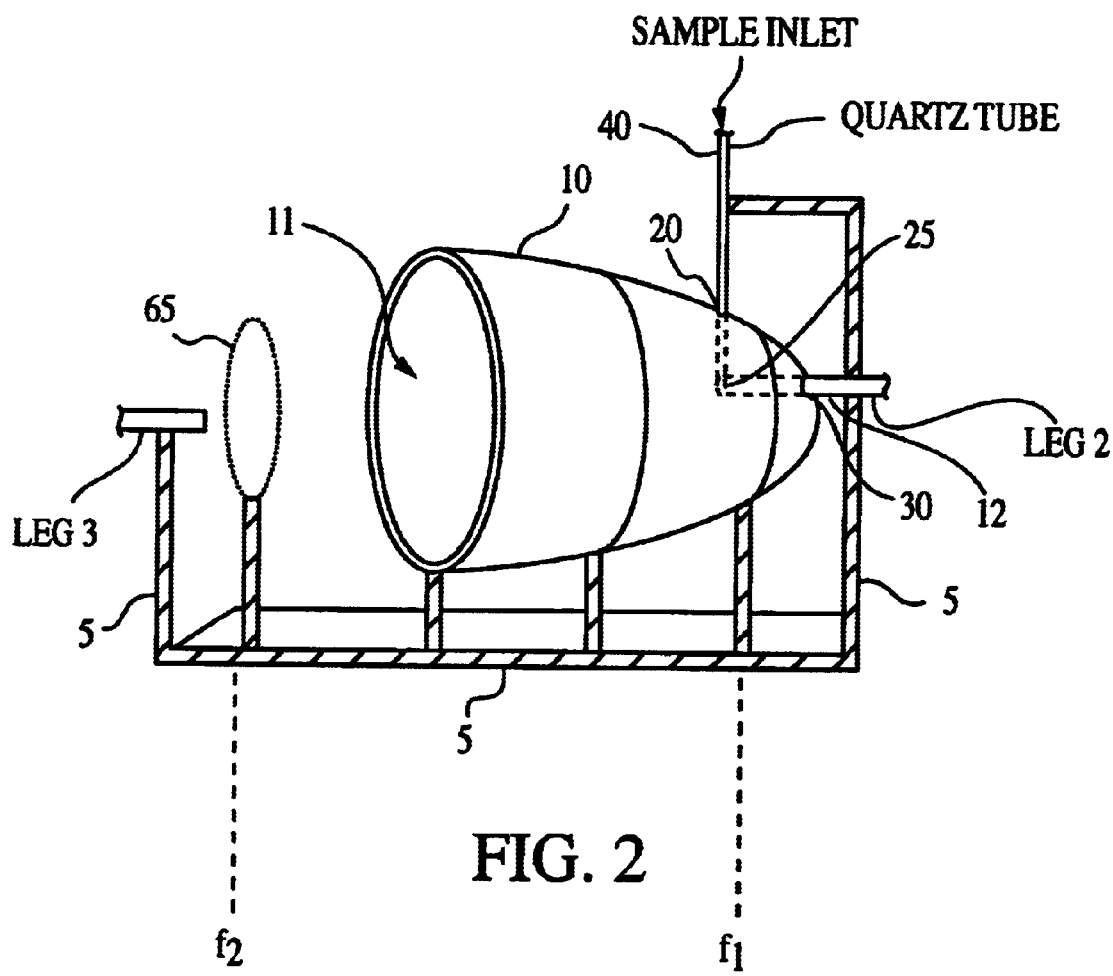
FIG. 2 shows a perspective view of a light collector device according to the present invention.

FIG. 2 shows a perspective view of a light collector device 100 according to the present invention. Capillary tube 40 is typically made of quartz. A rigid structure 5 is attached to the mirror 10 and to the terminal ends of the optical fibers in Legs 2 and 3. Rigid structure 5 is made of a solid material such as plastic or metal to provide support, alignment and proper location of the fibers in Legs 2 and 3 in relation to the mirror. The exact construction of the structure 5, which could be incorporated in an enclosure or comprise a stand is not critical so long as it is capable of providing proper alignment of the fiber optic legs in relation to the mirror.

Mirror 10 is a rigid structure typically made of aluminum having an ellipsoidal cavity coated with a high reflectivity coating such as silver, gold, chrome, or other such reflective material. The coating should be selected to optimize reflection of light in the spectrum of interest for the particular application. The ellipticity of mirror 10 is preferably relatively large for optimal light collection at the two focal points.

Some of the optical fibers comprising the four Legs shown in FIG. 1, which collect scattered light from the sample, typically have a relatively high numerical aperture, for example around 0.22, and can encompass a large core diameter, for example 200 microns. In particular, Leg 1 of the combined optical fiber bundle preferably comprises a single fiber that is coupled to the EM radiation source 80 at one end and delivers the light to the sample from its other end. Leg 1 can become a center fiber of a bundle of optical fibers that includes the center fiber of Leg 1 surrounded by the fibers for collection of light scattered from the source. For example, in FIG. 1, Leg 2 is shown in cross-section as eighteen collection fibers placed around the single fiber of Leg 1.

Leg 3 can be eighteen additional collection fibers placed in two concentric circular layers. This leg is placed at the second focal point $f_2$ of the mirror 10. Leg 4 is preferably a combination of the thirty-six collection fibers (eighteen fibers from Legs 2 and 3). Leg 4 is tightly packed and securely coupled to the spectrometric apparatus 60 for reliability in the field and ease of use in spectrometric applications. The electromagnetic energy source 80 can use either coherent or noncoherent light.

Very efficient collection of light is made possible by reflecting uncollected light scattered from the sample at $f_1$ on the inner surface of ellipsoidal mirror 10 arid collecting it at $f_2$ where it is collected by the optical fibers of Leg 3. Therefore, most of the scattered light is collected by the Legs 2 and 3 of collection optical fibers, each located at one of the two focal points. As light is delivered to the sample, it is scattered in a $4\pi$ solid angle. The Leg 2 collection fibers, which surround the delivery fiber, collect the backscattered light in a relatively small solid angle $\alpha$, while the most of the rest of the scattered light in solid angle $(4\pi-\alpha)$, travels to the mirror and is reflected back to be focused at the second focal point where the second fiber collection bundle comprising Leg 3 collects it. Thus, most of the light can be collected and delivered to a spectrometric apparatus 60, or alternatively to a detection device. For example, in the ideal case, if angle $\alpha$ has a value of $\pi/25$, signal collection improves approximately 100-fold. Moreover, the fiber bundle comprising Legs 1–4 makes the device very flexible and portable for use in either laboratory or field applications.

Thus, the invention provides much ease of use in either a laboratory or field setting to enable efficient light collection capabilities of an observed sample. This is particularly critical in situations where very low light levels or scattering phenomenon in low cross section exists (for example Raman scattering measurements).

Many modifications and variations of the present invention are possible in view of the above disclosure. For example, although the preferred mode of the optical fiber Legs 1–4 is in a common bundle configuration, individuated optical fibers can be used. Additionally, although the preferred mode of using the invention is to place collection fibers at both the focal points of the ellipsoidal mirror, the invention can be used in modified form where only Leg 3 of the light collection optical fibers is used without need of Leg 2 light collection fibers. Therefore to be understood, that within the scope of the appended claims, the to invention may be practiced otherwise than as specifically described.

We claim:

1. An accessory for illumination of a sample and collection of light therefrom, comprising:
   an ellipsoidal mirror having focal points $f_1$ and $f_2$;
   a first optical fiber leg comprising multiple fibers for conveyance of light both to and from the sample having a terminus positioned at or near $f_1$;
   a sample holder positioned at $f_1$;
   a second optical fiber for conveyance of light from the sample having a terminus positioned at or near $f_2$.

2. An accessory according to claim 1 further comprising a rigid structure for maintaining the fiber optic cables in fixed relation to the mirror.

3. An accessory for illumination of a sample and collection of light therefrom, comprising:
   a light source;
   an ellipsoidal mirror comprising a first focal point $f_1$ and a second focal point $f_2$;
   a first fiber optic cable, having a terminus positioned at or near $f_1$, comprising at least one optical fiber for transmission of light from the light source to the sample and at least one optical fiber for collecting light emitted from the sample;
   a second fiber optic cable, having a terminus positioned at or near $f_2$ for collection of light from the vicinity of $f_2$;
   a sample holder for positioning a sample at $f_1$.

4. An accessory according to claim 3 wherein the sample holder comprises a capillary tube.

5. An accessory according to claim 4 wherein the ellipsoidal mirror comprises an aperture for insertion of the capillary tube.

6. An accessory according to claim 3 wherein the sample holder comprises a sample chamber.

7. An accessory according to claim 3 further comprising a rigid structure for aligning and maintaining the fiber optic cables in fixed relation to the mirror.

8. A method for the efficient collection of light from a sample, comprising positioning a sample at a first focal point $f_1$ of an ellipsoidal mirror;
   conveying light to $f_1$ by a first fiber optic cable comprising at least one optical fiber for transmission of light from the light source to the sample and at least one optical fiber for collecting light emitted from the sample, having a terminus in the vicinity of $f_1$;
   collecting light emitted from the sample by the first optic fiber cable;
   collecting light emitted from the sample by a second fiber optic cable having a terminus positioned at or near $f_2$;
   maintaining the mirror and fiber optic cables in a fixed alignment.

9. A spectrometer comprising an accessory for illumination of a sample and collection of light therefrom, comprising:
   an ellipsoidal mirror having focal points $f_1$ and $f_2$;
   a first optical fiber leg comprising multiple fibers for conveyance of light both to and from the sample having a terminus positioned at or near $f_1$;
   a sample holder positioned at $f_1$;
   a second optical fiber for collection of light from the vicinity of $f_2$ having a terminus positioned at or near $f_2$.

10. A spectrometer according to claim 9 further comprising a rigid structure for maintaining the fiber optic cables in fixed relation to the mirror.

11. A spectrometer for illumination of a sample and collection of light therefrom, comprising:
    a light source;
    an ellipsoidal mirror comprising a first focal point $f_1$ and a second focal point $f_2$;

a first fiber optic cable, having a terminus positioned at or near $f_1$, comprising at least one optical fiber for transmission of light from the light source to the sample and at least one optical fiber for collecting light emitted from the sample;

a second fiber optic cable, having a terminus positioned at or near $f_2$ for collection of light from the vicinity of $f_2$;

a sample holder for positioning a sample at $f_1$.

* * * * *